United States Patent [19]

Bellak

[11] Patent Number: 4,844,091
[45] Date of Patent: Jul. 4, 1989

[54] METHOD FOR MONITORING A STATE OF BEING

[75] Inventor: Leopold Bellak, Larchmont, N.Y.

[73] Assignee: C.P.S. Inc., Larchmont, N.Y.

[21] Appl. No.: 148,758

[22] Filed: Jan. 26, 1988

[51] Int. Cl.⁴ .............................................. A61B 19/00
[52] U.S. Cl. ..................................... 128/744; 128/782
[58] Field of Search .................... 128/744, 774, 782

[56] References Cited

U.S. PATENT DOCUMENTS

| | | | |
|---|---|---|---|
| 1,842,323 | 1/1932 | Gluzek | 128/744 |
| 2,453,841 | 11/1948 | Gluzek | 128/744 |
| 2,986,140 | 5/1961 | Gardner et al. | 128/1 R |
| 3,213,851 | 10/1965 | Currea | 128/1 R |
| 4,180,059 | 12/1979 | Tiep | 128/782 |
| 4,641,661 | 2/1987 | Kalarickal | 128/744 |

FOREIGN PATENT DOCUMENTS

| | | | |
|---|---|---|---|
| 158336 | 10/1985 | European Pat. Off. | 128/744 |
| 841035 | 7/1949 | Fed. Rep. of Germany | 128/744 |

Primary Examiner—Max Hindenburg
Assistant Examiner—J. P. Lacyk
Attorney, Agent, or Firm—Herbert Dubno

[57] ABSTRACT

A state of a sensible subject such as a person, e.g. a pain state, is monitored utilizing an instrument which generates a sound of increasing harshness as an analog to the state of being as that state worsens. The device is used to quantitate the depression, anxiety, pain or other dysphoric condition experienced by the patient and allows comparison between states of the patient at different times.

3 Claims, 1 Drawing Sheet

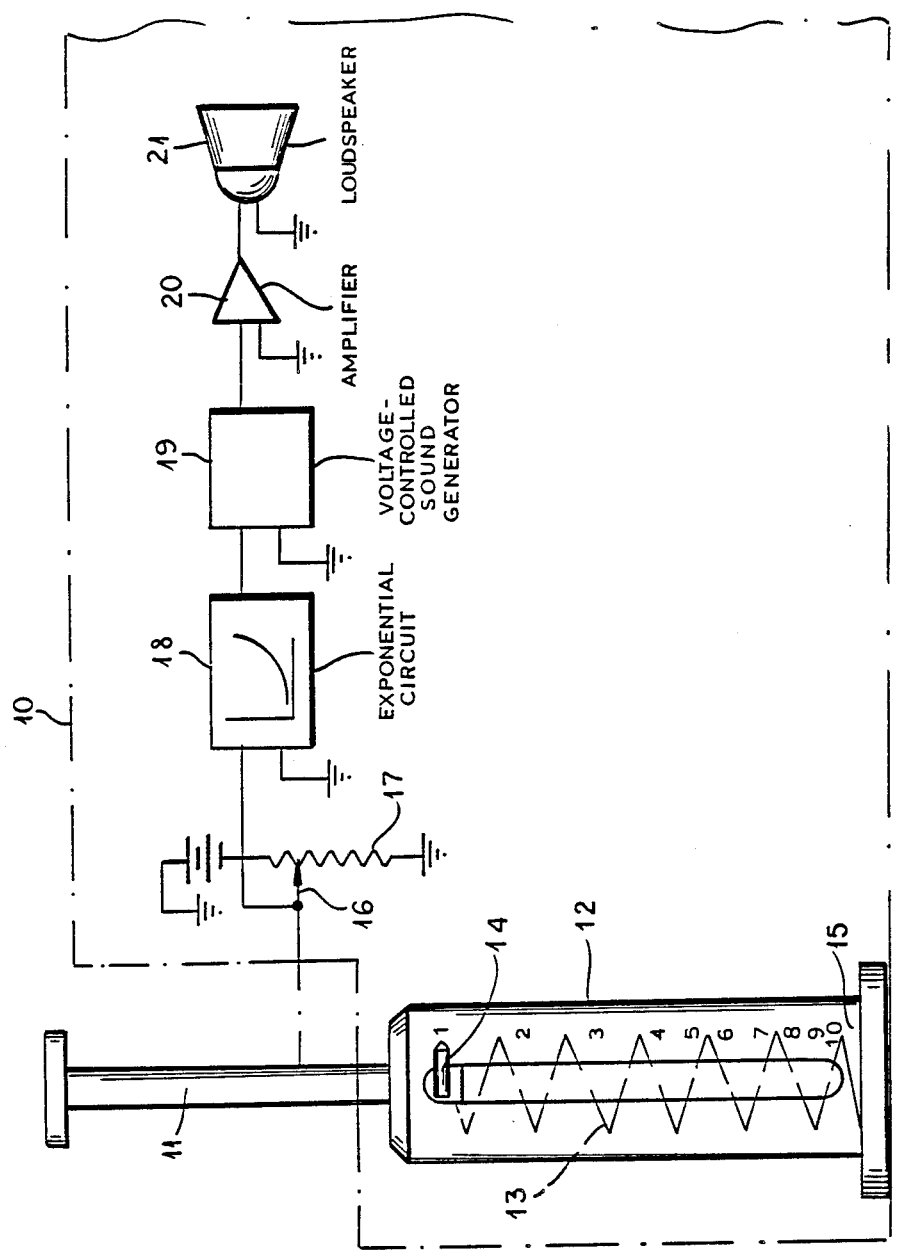

METHOD FOR MONITORING A STATE OF BEING

FIELD OF THE INVENTION

My present invention relates to a method of and to an apparatus for monitoring a state of being of a sensible subject, i.e. a subject capable of having a physical response to a stimulus which can be associated by the subject with an acoustic output so that subsequently the subject can signal a particular state of being by again generating a corresponding acoustic output. The invention is particularly directed to a device which can be described as a dysphorimeter, generally, or as a dolorimeter, when used as a pain-measuring system and to a method of operating same.

BACKGROUND OF THE INVENTION

The quantification of pain can be effected by various techniques. For example, in U.S. Pat. Ser. No. 2,453,841, a pressure is applied to the human body until the subject indicates that pain is felt and then a neutralizing pressure is applied close to the original site of pain application to relieve the pain and the levels of applied pressure can be quantified until a reproducible indication of the sensitivity of the subject to pain is obtained.

In U.S. Pat. Ser. No. 4,641,661, the point of a probe is pressed against the skin and acts upon a transducer which measures applied pressure. The subject can operate a switch when the pain thus generated reaches a threshold value and a digital indicator can then record the pressure of the transducer which will represent the pressure level at which the pain threshold is reached for that individual.

Mechanical skin-sensitivity detectors are described in U.S. Pat. Ser. Nos. 1,637,421 and 2,704,539.

In general a variety of techniques have been utilized in the field of biofeedback and elsewhere to associate particular stimulus with a sensation to which the patient may be sensitive.

However, in spite of the developments in these fields to date, there has yet to be provided a device or method which can provide a quantitative indication to a third party, hereinafter referred to as an observer, of a state of being of a subject such that the state of being can be quantified effectively and reproducibly.

OBJECTS OF THE INVENTION

It is the principal object of the present invention to provide an improved method of monitoring the state of being of a sensible subject which is free from the drawbacks of earlier techniques and can provide a highly reliable and yet relatively simple indication of the state of being of the patient or subject.

Another object of this invention is to provide an improved apparatus for carrying out this method.

SUMMARY OF THE INVENTION

These objects and others which will become apparent hereinafter are attained, in accordance with the present invention, in a method of monitoring a state of a sensible subject which comprises generating an acoustic analog representing a state of being of the patient by actuating a member causing the emission of a sound in a range of standard sounds extending from a pleasant tonality or sonority at one end of the range to an unpleasantly harsh tonality or sonority at the opposite end of the range so that the degree of unpleasantness of the sound generated is associated with the degree of dysphoria sensed by the patient or subject. The range of standard sounds is associated with a range of numerical values, permitting the physician to assign numerical values to the generated sounds representing the degree of the dysphoria. Since the subject can be his or her own control, by comparing the numerical values associated with the sounds generated by the patient to represent the particular degree of dysphoria (e.g. depression, anxiety, pain), the physician, therapist or other health-care professional can readily compare the different states of being, develop a meaningful history or judge the effect of treatment.

Generally speaking, for a determination of mental states which are not associated with direct stimuli, the device is effective when operated by the subject or patient with an instruction to depress an actuator until the nature of the sound produced best represents the subject's feeling as an analog to the depression or anxiety level, for example. Usually, the subject will then depress the actuator to a greater and lesser extent, hunting for the sound characteristic which would satisfy this criterium.

In the case of pain and other dysphoric states which can be induced, a standardization of the associations of generated sounds with the state of the subject can be developed initially over a range of states.

Hence, in another aspect of the invention, the method comprises administering to the subject a physical or emotional stimulus capable of altering a state of being of the subject and varying with time. The subject is caused to generate a spectrum of sounds by transducing a physical movement of the subject into an acoustical output in response to the stimulus from a range of standard sounds extending from a pleasant tonality at one end of the range to an unpleasantly harsh tonality at an opposite end of the range, whereby a particular sound from the range generated by the subject represents a particular state of the subject caused by the varying stimulus and the subject identifies the particular sound with the particular state of being.

Thereafter the state of being of the patient is quantitatively determined and signaled to the observer by the generation of a sound corresponding to the sound from the range which the subject has identified or associated with that particular state of being.

Preferably numerical values are assigned to the sounds of the range forming the spectrum and during the assignment of sounds to particular states of being, the numerical values are recorded so that, when later the subject generates a particular sound, the corresponding numerical value will be meaningful to the observer as representing a particular state of being of the patient. Most commonly the state of being is a state of depression, anxiety and pain and other dysphorias and the spectrum of sounds is generated by having the subject press upon an actuator, the subject thereafter displaying a degree of pain which the person may be experiencing by pressing on the same or a corresponding actuator until a level of the sound is generated by correspondence to a sound of the original spectrum associated with a corresponding degree of pain generated by the stimulus.

The apparatus of the invention, of course, includes the means for displaying the numerical values associated with the actuator and, of course, the sound-generating means or transducer which is required to practice the method.

While the invention has been generally described as being capable of quantifying pain, it may be used for the quantitation of other emotional states such as depression, anxiety and like dysphorias. The system uses a scale on which the response to the subject can be displayed, generally a numerical scale, with increasing values to the extent that the dysphoric state or pain approaches the more extreme levels. Associated with the range of numerical values is a range of acoustic outputs which become increasingly unpleasant because of amplitude, pitch, harmonics, noise or all of these parameters, as the numerical values increase.

In applying the invention to dental treatment, the original stimulus may be the action of a dental drill or other like pain-generating activity, for example the application of pressure pain or a pin or needle, e.g. utilizing any of the sensitivity-generating devices described in the prior art as developed above.

Once the patient has associated a variety of sounds within the range outputted by the transducer with particular levels of pain and there has been a quantification by the observer, e.g. a dentist, by the recording of the numerical values associated with the acoustic responses, the patient, although unable to speak because of manipulative activity in the mouth, can nevertheless signal the degree of pain being experienced by pressing upon the actuator until he or she recognizes the resulting sound generated as representing the level of pain previously experienced and associated with that sound. The patient thus matches pain by matching the sounds and the observer can readily ascertain by the numerical value and the sound being generated by the patient during the dental procedure, the degree of pain to which that patient is subject.

Of course, the applicability of this invention to a dental procedure has been given only by way of example. The invention is equally applicable to arthritic pain of the shoulder, abdominal discomfiture and any other painful experience. It can be used for signalling anxiety, clinical discomfort in internal medicine and in psychiatry for indicating anxiety, depression and dysphoria generally.

The instrument and method of the invention may be used for measuring the effect of drugs on a patient, for example, in testing the value of analgesics, a statistically significant number of subjects may be given standard stimuli to develop specific acoustical responses and then broken into control and test groups to whom the analgesic may be administered. The repeated tests can demonstrate the increased ability of the patient receiving the analgesic to experience pain.

For an individual patient, the device and method may be used to test a particular patient's response to a particular drug. i.e. to provide a quantitative indication as to whether an analgesic can have an effect on a pain state of that patient.

The actuator may be any type of subject-operated device, e.g. a plunger which can be depressed by the index finger of the subject and connected to a system which outputs a more dissonant and unpleasant sound, the more that the plunger is depressed. The plunger may be provided with a scale which can be logarithmic or bear some other nonlinear relationship to the pain experienced by the patient, the plunger being coupled to a means for generating a sound of increasing unpleasantness. In the 1 position of the plunger, no sound may be emitted and at full scale, say 10, an extremely raucous sound may be generated.

As the patient depresses the plunger until he is able to associate an emitted sound with a sound known to him to represent his particular pain level, the physician or other observer can record the number of the scale at which the plunger is halted for the particular level of pain experienced by the patient. The physician can record that number and compare it with prerecorded values from other occasions so that a patient's history, response to drugs or the like can be developed.

BRIEF DESCRIPTION OF THE DRAWING

The above and other objects, features and advantages of the present invention will become more readily apparent from the following description, reference being made to the accompanying drawing, the sole FIGURE of which is a diagram illustrating an instrument for carrying out the method of the invention.

SPECIFIC DESCRIPTION

In the drawing I have shown an instrument which can be contained in a common housing represented diagrammatically at 10 and can comprise a plunger 11 displaceable in a cylinder 12 against the force of a spring 13 so that a pointer 14 on the plunger can signal or display the degree of depression of the plunger on a nonlinear scale 15.

In the dolorimeter shown in the drawing, the 1-10 scale 15 illustrated is an ordinal scale which can be similar to the commonly used hardness scale, namely the Mohs' scale. It can, however, be any other ordinal scale such that the distances between the gradients need not be equal or even linearly proportional as in a standard metric scale. In the preferred case, a logarithmic scale may be used so that each increment of the scale represents a greater increase in the particular state than a preceding increment. For the measurement of pain, anxiety, or depression, 2 can represent greater pain than 1, 3 a greater pain level than 2, etc.

The transduction of the depression of the plunger 11 to an acoustic output with increasing harshness of sound can be effected by any desired transducer arrangement. For example, the plunger can be coupled to a reed-type sound generator with depression of the plunger generating increased screech as the plunger depth increases. Preferably, however, an electronic transducer system is provided and, in that case, the plunger 11 can be coupled to the wiper 16 of a potentiometer 17 whose output voltage is delivered to an exponential circuit 18, i.e. a circuit having an exponential transfer function so that the voltage output of this circuit increases exponentially with the voltage input.

The output voltage from the circuit 18 is applied to a voltage-controlled sound generator 19 with an output whose frequency and harmonic (noise) level increases with increasing input voltage. The circuit 19 can be provided with a voltage-controlled oscillator for that purpose. The output of circuit 19 is applied to an amplifier 20 and then to the loudspeaker 21.

In ascertaining the patient's response initially, the physician can apply the stimulus to the patient either in the form of pain by a needle or some other stimulation, such as forced excursion of a limb, etc. The patient depresses the plunger 11 with increasing sensation of pain and the depression of the plunger generates a sound at the loudspeaker 21 whose raucousness increases with increasing depression of the plunger and increasing sensation of pain. The physician may record the numerical values signalled by the pointer 14 for each level of pain experienced by the subject.

The patient, of course, associates the particular sound with a particular level of pain so that at a later date, when that patient must demonstrate to the physician the degree of pain which the patient may be experiencing, he need merely depress the plunger until the sound generated by the loudspeaker again reads the pain level so that the physician will then have a quantitative measurement of the pain experienced by that patient from the reading on the scale. Alternatively, the instrument may be used in the various ways described to demonstrate the particular pain level which the patient may be experiencing at any time for comparison with a prior state.

I claim:

1. A method of monitoring an emotional state of a person, comprising the steps of:
    (a) administering to a person whose emotional state is to be monitored a stimulus affecting the emotional state of said person and allowing said person to react to said stimulus;
    (b) causing said person to displace voluntarily an actuator in response to the reaction of said person to said stimulus;
    (c) generating upon the displacement of said actuator a continuous acoustical output with tonality of increasing stridency with increasing displacement of said actuator so that said person will identify an emotional state resulting from said stimulus with a particular acoustic output and degree of displacement of said actuator;
    (d) displaying the movement of said actuator upon a numerical scale and recording values thereof to quantitate the person's emotional state; and
    (e) thereafter signalling a subsequent emotional state of said person by causing said person to displace voluntarily said actuator until the acoustic output reaches a level associated by the person with said subsequent emotional state and displaying the movement of said actuator associated with the subsequent emotional state upon a numerical scale, whereby the numerical value of the subsequent emotional state is evaluated with respect to said recorded values to determine the person's current emotional state.

2. The method defined in claim 1 wherein said emotional state is a dysphoric state and said stimulus is a psychiatric stimulus.

3. The method defined in claim 1 wherein, in step (d), the displacement of said actuator is displayed against an ordinal scale.

* * * * *